United States Patent [19]

Franckowiak et al.

[11] Patent Number: 4,876,254

[45] Date of Patent: Oct. 24, 1989

[54] CIRCULATION-ACTIVE SUBSTITUTED 5-NITRO-1,4-DIHYDROPYRIDINES

[75] Inventors: Gerhard Franckowiak, Wuppertal; Michael Kayser, Leverkusen; Matthias Schramm, Cologne, all of Fed. Rep. of Germany; Günther Thomas, Arese, Italy; Rainer Gross, Wuppertal, Fed. Rep. of Germany; elisabeth Perzborn, Wuppertal, Fed. Rep. of Germany; Friedel Seuter, Wuppertal, Fed. Rep. of Germany

[73] Assignee: Bayer Aktiengesellschaft, Leverkusen, Fed. Rep. of Germany

[21] Appl. No.: 179,102

[22] Filed: Apr. 8, 1988

[30] Foreign Application Priority Data

Apr. 11, 1987 [DE] Fed. Rep. of Germany ....... 3712369

[51] Int. Cl.[4] .................... C07D 401/12; A61K 31/50
[52] U.S. Cl. .................................. 514/252; 544/238; 544/239
[58] Field of Search ................. 544/238, 239; 514/252

[56] References Cited

U.S. PATENT DOCUMENTS

| | | | |
|---|---|---|---|
| 4,705,794 | 11/1987 | Wehinger et al. | 544/238 |
| 4,707,479 | 11/1987 | Meyer et al. | 544/238 |
| 4,777,256 | 10/1988 | Veda et al. | 544/238 |

FOREIGN PATENT DOCUMENTS

| | | |
|---|---|---|
| 3311005 | 9/1984 | Fed. Rep. of Germany . |
| 3339861 | 5/1985 | Fed. Rep. of Germany . |
| 3431862 | 3/1986 | Fed. Rep. of Germany . |
| 3445852 | 6/1986 | Fed. Rep. of Germany . |

*Primary Examiner*—Nicholas S. Rizzo

*Attorney, Agent, or Firm*—Sprung Horn Kramer & Woods

[57] ABSTRACT

For the treatment of circulation disorders, the novel 5-nitro-1,4-dihydropyridines of the formula

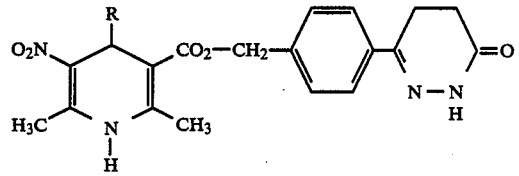

in which
R represents $C_6$–$C_{14}$-aryl which can be mono- to pentasubstituted by identical or different substituents from the series comprising halogen, nitro, cyano, $C_1$–$C_6$-alkyl, $C_1$–$C_6$-alkoxy, $C_1$–$C_6$-alkoxy, $C_1$–$C_6$-alkylthio, trifluoromethyl, trifluoromethoxy, difluoromethoxy, trifluoromethylthio and benzyl, benzyloxy or benzylthio optionally substituted by nitro, cyano, trifluoromethyl, $C_1$–$C_4$-alkyl or $C_1$–$C_4$-alkoxy, or represents a heterocycle from the series pyrryl, thienyl, furyl, pyrazolyl, imidazolyl, oxazolyl, thiazolyl, pyridyl, pyridazinyl, pyrimidyl, quinolyl, benzoxadiazolyl, chromenyl or thiochromenyl optionally mono- to tetrasubstituted by halogen, phenyl or $C_1$–$C_4$-alkyl or represents straight-chain, branched or cyclic alkyl with up to 14 carbon atoms, and their physiologically acceptable salts.

13 Claims, No Drawings

CIRCULATION-ACTIVE SUBSTITUTED 5-NITRO-1,4-DIHYDROPYRIDINES

The invention relates to substituted 5-nitro-1,4-dihydropyridines, several processes for their preparation and their use in medicaments, in particular for the control of circulatory disorders.

The present invention relates to substituted 5-nitro-1,4-dihydropyridines of the general formula (I)

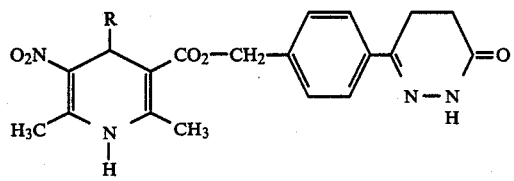
(I)

in which
R represents $C_6-C_{14}$-aryl which can be mono- to penta-substituted by identical or different substituents from the series comprising halogen, nitro, cyano, $C_1-C_6$-alkyl, $C_1-C_6$-alkoxy, $C_1-C_6$ alkylthio, trifluoromethyl, trifluoromethoxy, difluoromethoxy, trifluoromethylthio and benzyl, benzyloxy or benzylthio optionally substituted by nitro, cyano, trifluoromethyl, $C_1-C_4$-alkyl or $C_1-C_4$-alkoxy, or represents a heterocycle from the series pyrryl, thienyl, furyl, pyrazolyl, imidazolyl, oxazolyl, thiazolyl, pyridyl, pyridazinyl, pyrimidyl, quinolyl, benzoxadiazolyl, chromenyl and thiochromenyl which is optionally mono- to tetrasubstituted by halogen, phenyl or $C_1-C_4$-alkyl, or represents straight-chain, branched or cyclic alkyl with up to 14 carbon atoms, and their physiologically acceptable salts.

Compounds of the general formula (I) are preferred in which

R represents phenyl or naphthyl, which can be mono- to tetrasubstituted by identical or different substituents from the series comprising fluorine, chlorine, bromine, nitro, cyano, $C_1-C_4$-alkyl, $C_1-C_4$-alkoxy, $C_1-C_4$-alkylthio, trifluoromethyl, difluoromethoxy, tri-fluoromethoxy, trifluoromethylthio, and benzyloxy or benzylthio optionally substituted by nitro, fluorine, chlorine, bromine, trifluoromethyl, methyl or methoxy, or represents a heterocycle from the series thienyl, furyl, pyridyl, pyrimidyl, quinolyl, benzoxadiazolyl and thiochromenyl, optionally mono- to trisubstituted by methyl, fluorine, chlorine, bromine or phenyl, or represents straight-chain, branched or cyclic alkyl with up to 12 carbon atoms, and their physiologically acceptable salts.

Compounds of the general formula (I) are particularly preferred in which

R represents phenyl, which can be mono- to trisubstituted by identical or different substituents from the series comprising fluorine, chlorine, nitro, cyano, $C_1-C_4$-alkyl, $C_1-C_4$-alkoxy, trifluoromethyl, trifluoromethoxy, and benzyloxy or benzylthio optionally substituted by nitro, fluorine, chlorine, bromine, trifluoromethyl, methyl or methoxy, or represents thienyl, furyl, pyridyl or benzoxadiazolyl, or represents a heterocycle of the formula

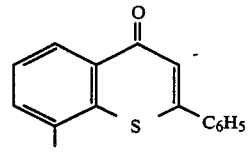

represents cyclic alkyl with up to 10 C atoms such as cyclohexyl or adamantyl, and their physiologically acceptable salts.

Physiologically acceptable salts are salts of the compounds according to the invention with inorganic or organic acids. These preferably include inorganic acids such as hydrohalic acids, preferably HCl or HBr, sulphuric acid, phosphoric acid, or organic carboxylic acids or sulphonic acids such as, for example, acetic acid, maleic acid, fumaric acid, malic acid, citric acid, tartaric acid, lactic acid, benzoic acid, methanesulphonic acid, ethanesulphonic acid, benzenesulphonic acid, naphthalenedisulphonic acid or toluenesulphonic acid.

The compounds according to the invention exist in stereoisomeric forms, which behave either as image and mirror image (enantiomers) or not as image and mirror image (diastereomers). The invention relates both to the antipodes and to the racemic forms and also to the diastereomeric mixtures. Like the diastereomers, the racemic forms can also be separated into the stereoisomerically uniform constituents in a known manner (cf. E. L. Eliel, Stereochemistry of Carbon Compounds, McGraw Hill, 1962).

The compounds according to the invention of the general formula (I) are prepared by reacting [A] aldehydes of the general formula (II)

in which
R has the meaning given above, with nitroacetone of the formula (III)

and the enamine of the formula (IV)

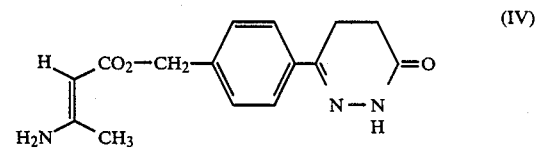
(IV)

in the presence of inert solvents, or by reacting
[B] aldehydes of the general formula (II) with the ketone of the formula (V)

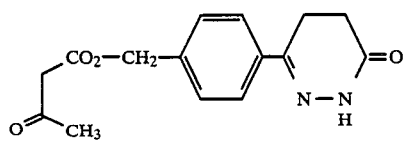

and the enamine of the formula (VI)

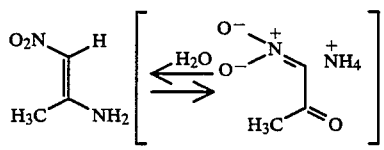

in the presence of inert solvents, or by reacting

[C] nitroacetone (III) with ammonia and ylidene compounds of the general formula (VII)

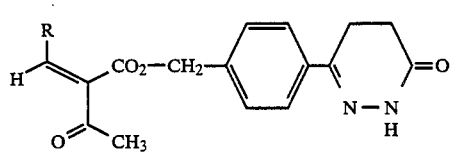

in which

R has the meaning given above, in the presence of inert solvents, or by reacting,

[D] the ketone of the formula (V) with ammonia and ylidene compounds of the general formula (VIII)

in which

R has the meaning given above, in the presence of inert solvents, or by reacting

[E] the enamine of the formula (VI) with ylidene compounds of the general formula (VII) in the presence of inert solvents, or by reacting

[F] the enamine of the formula (IV) with ylidene compounds of the general formula (VII) in the presence of inert solvents, or by esterifying

[G] 1,4-dihydropyridinecarboxylic acids of the general formula (X)

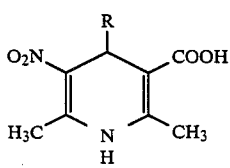

in which

R has the meaning given above, according to the usual methods for the esterification of carboxylic acids (for example via the acid chloride or imidazolide or in the presence of dicyclohexylcarbodiimide) with the alcohol of the formula (XI)

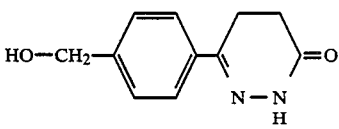

Depending on the type of the starting compounds employed the process variations A–F can be illustrated by the following schemes:

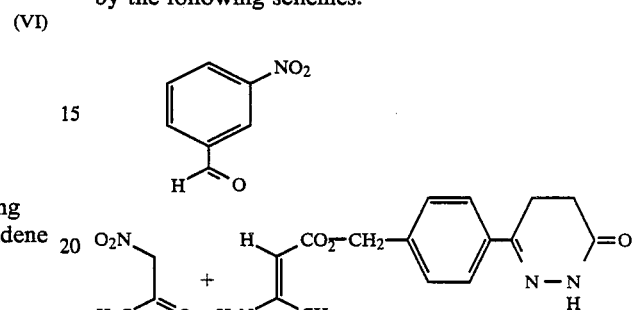

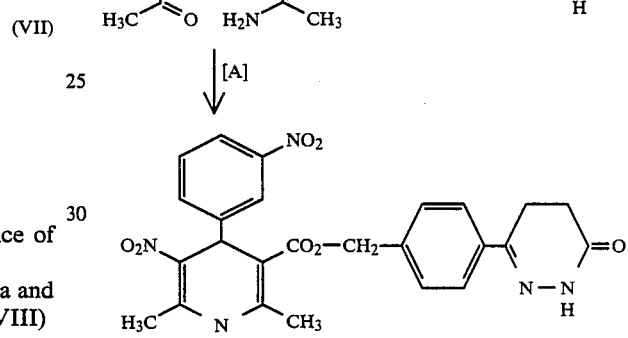

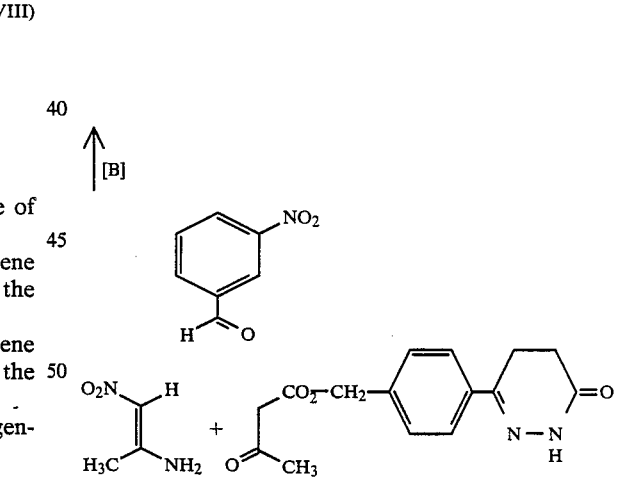

The aldehydes of the general formula (II) employed as starting substances are known or can be prepared by known methods [E. Mosettig, Organic Reactions III, 218 (1954); E. P. Papadopoulos, A. Jarrar, C. H. Isidorides, J. Org. Chem. 31, 615 (1966); Mijano et al., Chemical Abstracts 59, 13 929 (1963); A. J. Mancuso, D. S. Brownfain, D. Swern, J. Org. Chem. 44, 4148 (1979); T. D. Harris, G. P. Roth, J. Org. Chem. 44, 2004 (1979)].

The nitroacetone (III) is known and can be prepared by known methods [N. Levy, C. W. Scaife, J. Chem. Soc. 1949, 1100; C. D. Hurd, M. E. Nilson, J. Org. Chem. 20, 927 (1955), G. F. Field, W. J. Zally, Synthesis 295 (1979)].

The ketone of the formula (V) employed as a starting substance can be prepared by known methods [D. Borrmann, in Houben-Weyls "Methoden der organischen Chemie" ("Methods of Organic Chemistry") VII/4, 230 (1968)].

The enamines of the formulae (IV) and (VI) employed as starting substances are known or can be prepared by known methods [S. A. Glickman, A. C. Cope, J. Am. Chem. Soc. 67, 1017 (1945); H. Böhme, K.-H. Waisel, Arch. Pharm. 310, 30 (1977)].

The ylidene compounds of the general formulae (VII) and (VIII) employed as starting substances are known in part or can be prepared by known methods [E. Jones, Organic Reactions XV, 204 (1967); A. Dornow, W. Sassenberg, Liebigs Am. Chem. 602, 14 (1957)].

The carboxylic acids of the formula (X) employed as starting substances are known or can be prepared according to known methods [German Pat. No. 3,206,671].

PROCESS VARIATIONS A-F

Water and all inert organic solvents which are not altered by the reaction conditions can be used as solvents for processes A-F. These preferably include alcohols such as methanol, ethanol, propanol, isopropanol, ethers such as diethyl ether, dioxane or tetrahydrofuran, dimethylformamide, dimethyl sulphoxide, acetonitrile, glacial acetic acid, ethyl acetate, hexamethylphosphoric triamide, or hydrocarbons such as benzene, toluene or xylene. Mixtures of the mentioned solvents can likewise be employed.

The reaction temperatures for all processes can be varied within a relatively large range. In general temperatures of +10° C. to +200° C., preferably of +20° C. to 150° C., are used, in particular the boiling temperature of the solvent employed.

The reaction can be performed under atmospheric pressure, but also under increased or reduced pressure. In general atmospheric pressure is used.

In carrying out the process according to the invention the ratio of the substances participating in the reaction is optional. In general molar quantities of reactants are used. In processes C and D it has proved suitable to use ammonia in an excess of up to 200 fold, preferably in an excess of up to 10 fold.

PROCESS VARIATION G

The performance of process variation G according to the invention relies on the method for the esterification of carboxylic acids which is known from the literature. In this method the carboxylic acid is first converted into an activated form, such as, for example, the acid chloride or the imidazolide, which is either isolated as such and converted in a second reaction step or alkanolated directly to the compounds according to the invention in situ. In addition to the inorganic halides such as thionyl chloride, phosphorus trichloride or phosphorus pentachloride, carbonyldiimidazole, carbodiimides such as dicyclohexylcarbodiimide or 1-cyclohexyl-3-[2-(N-methylmorpholino)-ethyl]carbodiimide p-toluenesulphonate or N-hydroxy-phthalimide or N-hydroxybenzotriazole in the presence of dicyclohexylcarbodiimide may be mentioned as examples of activating agents. Naturally the 1,4-dihydropyridine monocarboxylic acids can also be converted into salts, which can be reacted with substrates of the general formula (XII)

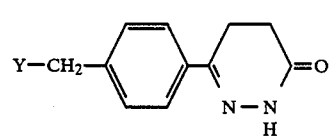

in which
Y represents a nucleofugic group such as, for example, iodide or tosylate, to give the compounds according to the invention.

All inert organic solvents are suitable as diluents. These preferably include ethers such as dioxane, tetrahydrofuran, glycol monomethyl ether or glycol dimethyl ether, halogenated hydrocarbons such as dichloromethane or trichloromethane, dimethylformamide, dimethyl sulphoxide, acetonitrile, pyridine and hexamethylphosphoric triamide. If the activated intermediate stages of the 1,4-dihydromonocarboxylic acids are isolated, then the alcohol of the formula (XI) can also be employed alone as a diluent.

The alkanolysis is advanntageously accelerated by addition of catalytic or molar amounts of a basic auxiliary.

The reaction temperatures can be varied within a relatively large range. In general temperatures between +10° C. and +200° C., especially between +20° C. and +150° C., are used, preferably, however, the boiling temperature of the particular solvent.

The reaction can be carried out under normal pressure, but also under increased pressure. In general normal pressure is used.

The compounds according to the invention influence the contractility of the heart and the smooth muscle tone. They can therefore be employed in medicaments for influencing pathologically altered blood pressure, as coronary therapeutic agents and in the treatment of cardiac insufficiency. Moreover, they can be used for the treatment of arrhythmias, for lowering blood sugar, for detumescing the mucous membranes and for influencing the salt and liquid balance.

The cardiac and vascular activities were discovered using isolated perfused guineapig hearts.

The hearts of guineapigs weighing 250 to 350 g are used for this purpose. The animals are killed by a blow to the head, the thorax is opened, and a metal cannula is tied into the exposed aorta. The heart is removed from the thorax with the lungs and is connected to the perfusion apparatus via an aortic cannula for continuous perfusion. The lungs are separated at the roots of the lungs. A Krebs-Henseleit solution (1) (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$, 0.013 mmol/l of $Na_2EDTA$), which contains 1.2 mmol/l of $CaCl_2$, is used as the perfusion medium. 10 mmol/l of glucose are added as an energy-supplying substrate. Upstream of the perfusion the solution is filtered to remove particles. The solution is gassed with Carbogen (95% $O_2$, 5% $CO_2$) in order to maintain a pH value of 7.4. The hearts are perfused at a constant flow rate (10 ml/min) at 32° C. using a peristatic pump.

In order to measure the cardiac function a latex balloon filled with liquid, which is connected via a column of liquid to a pressure gauge, is introduced into the left ventricle through the left auricle, and the isovolumetric contractions are recorded on a high-speed recorder (Opie, L., J. Physiol. 180 (1965) 529–541). The perfusion pressure is recorded by means of a pressure gauge which is connected to the perfusion system upstream of the heart. Under these conditions a decrease in the perfusion pressure indicates coronary dilatation, and a rise or fall in the amplitude of contraction of the left ventricle indicates an increase or decrease in cardiac contractility. The compounds according to the invention are infused into the perfusion medium at suitable dilutions shortly upstream of the isolated heart.

The figures which follow show, as an example, the effect of the compounds according to the invention on isolated perfused guineapig hearts, expressed as the percentage difference from the initial figure equated with 100%.

| Example No. | Concentration (g/ml) | % change in contractility | % change in perfusion pressure |
|---|---|---|---|
| 2 | $10^{-6}$ | +22 | −35 |
| 3 | $10^{-6}$ | +6 | 0 |
| 4 | $10^{-6}$ | +63 | −35 |
| 5 | $10^{-6}$ | +102 | −45 |
| 6 | $10^{-6}$ | +48 | −11 |
| 7 | $10^{-6}$ | +56 | −22 |
| 8 | $10^{-6}$ | +5 | −21 |
| 9 | $10^{-6}$ | +16 | −10 |
| 11 | $10^{-6}$ | +35 | −37 |
| 12 | $10^{-6}$ | +70 | −25 |
| 13 | $10^{-6}$ | +6 | −10 |
| 14 | $10^{-6}$ | +15 | −6 |
| 15 | $10^{-6}$ | +22 | −14 |
| 18 | $10^{-6}$ | +46 | 0 |
| 22 | $10^{-6}$ | +78 | −10 |
| 23 | $10^{-6}$ | +40 | 0 |
| 25 | $10^{-6}$ | +72 | 0 |
| 27 | $10^{-6}$ | +28 | −10 |
| 28 | $10^{-6}$ | +9 | −16 |

Furthermore, the substances of the formula (I) according to the invention act as inhibitors/stimulators of enzymatic reactions in the context of arachidonic acid metabolism. Such substances are suitable for the prophylaxis and treatment of disorders of the respiratory tract such as emphysema, shock lung, pulmonary hypertension, oedema, thrombosis and thromboembolism, ischaemia (peripheral, coronary, cerebral circulatory disturbances), coronary and cerebral infarctions, dysrhythmias, angina pectoris, hypertension and also arteriosclerosis. The substances according to the invention act preferentially as inhibitors of thromboxane synthesis.

THROMBOCYTE AGGREGATION

Thrombocytes and their adhesion and aggregation capability are an essential pathogenetic factor in the formation of thromboses, particularly in the arterial branch of the vascular system.

For the determination of thrombocyte aggregation inhibitory activity, blood from healthy subjects of both sexes was used. 9 parts of blood were admixed to one part of 3,8% strength aqueous sodium citrate solution as an anti-coagulant. Platelet-rich citrate plasma (PRP) was obtained from this blood by means of centrifugation (Jurgen/Beller, Klinische Methoden der Blutgerinnungsanalyse (Clinical Methods of Blood Coagulation Analysis); Thieme Verlag, Stuttgart, 1959).

For these studies 0.8 ml of PRP and 0.1 ml of the active substance solution were pre-incubated at 37° C. in a waterbath. Thrombocyte aggregation was then determined at 37° C. in an aggregometer (Therapeutische Berichte 47, 80–86, 1975) using the turbidometric method (Born, G. V. R., J. Physiol. (London), 162, 67, 1962). Aggregation was induced by adding 0.1 ml of collagen, an aggregation inducing agent.

The alteration of the optical density in the PRP sample was recorded during a 4 minute period and the divergence after 4 minutes was determined. For this purpose the percentage inhibition compared with the control was calculated.

The range of the minimal effective concentrations is given as a limiting concentration (Table 2).

Collagen-induced thrombocyte aggregation

| Example No. | Limiting concentrations (μg/ml) |
|---|---|
| 3 | 1–0.3 |
| 6 | 10–3 |
| 7 | 3–1 |
| 8 | 3–1 |
| 9 | 3–1 |
| 11 | 3–1 |
| 12 | 3–1 |
| 14 | 1–0.3 |

The new active compounds can be converted in a known manner into the customary formulations, such as tablets, dragees, pills, granules, aerosols, syrups, emulsions, suspensions and solutions, using inert, non-toxic, pharmaceutically suitable excipients or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example when water is used as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol), excipients, such as, for example, natural rock powders (for example kaolins, aluminas, talc and chalk), synthetic rock powders (for example highly disperse silica and silicates), sugars (for example sucrose, lactose and glucose), emulsifiers (for example polyoxyethylene fatty acid esters, polyoxyethylene fatty alcohol ethers, alkylsulphonates and arylsulphonates), dispersing agents (for example ligninsulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, particularly perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc, can be co-used when making tablets. In the case of aqueous suspensions the active compounds can be mixed with various flavor improving agents or colorants in addition to the abovementioned auxiliary substances.

In the case of parenteral use, solutions of the active compounds, employing suitable liquid excipients, can be used.

In general, it has proved advantageous, in the case of intravenous administration, to administer amounts of about 0.001 to 1 mg/kg, preferably about 0.01 to 0.5 mg/kg, of body weight daily to achieve effective results, and in the case of oral administration, the dosage is about 0.01 to 20 mg/kg, preferably 0.1 mg to 10 mg/kg, of body weight daily.

Nevertheless, it can at times be necessary to deviate from the amounts mentioned, and in particular to do so as a function of the body weight or of the nature of the administration method, of the individual behavior towards the medicament, and the nature of the formulation of the medicament and the time at which or interval over which the administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day.

PREPARATION EXAMPLES

Example 1

4-(6-Oxo-1,4,5,6-tetrahydropyridazin-3-yl)benzyl 1,4-dihydro-2,6-dimethyl-4-(4-nitrophenyl)-5-nitropyridine-3-carboxylate

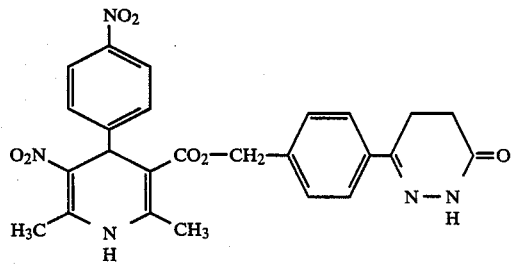

20 mmol of 2-nitro-1-(2-trifluoromethylphenyl)butan-3-one are heated at reflux for 6 hoiurs with 20 mmol of 4-(6-oxo-1,4,5,6-tetrahydropyridazin-3-yl)benzyl β-aminocrotonate in 40 ml of i-propanol. After partial evaporation of the solvent, the product precipitates as crystals.

Melting point: 224° C.
Yield: 64% of theory

Example 2

4-(6-Oxo-1,4,5,6-tetrahydropyridazin-3-yl)benzyl 4-(3-benzyloxyphenyl)-1,4-dihydro-2,6-dimethyl-5-nitropyridine-3-carboxylate

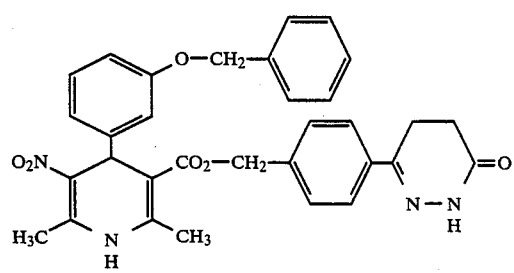

10 mmol of 3-benzyloxybenzaldehyde and 10 mmol of 4-(6-oxo-1,4,5,6-tetrahydropyridazin-3-yl)benzyl 3-aminocrotonate are heated at 60° C. for 8 hours in 30 ml of i-propanol, a total of 20 mmol of nitroacetone being added in portions. The product crystallizes after addition of a little petroleum ether and trituration. It is recrystallized from a little i-propanol.

Melting point: 134° C.
Yield: 42% of theory

Example 3

4-(6-Oxo-1,4,5,6-tetrahydropyridazin-3-yl)benzyl 4-(3-chlorophenyl)-1,4-dihydro-2,6-dimethyl-5-nitropyridine-3-carboxylate

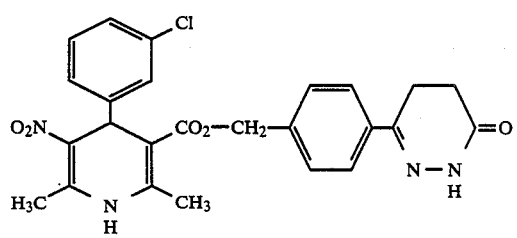

10 mmol of 4-(3-chlorophenyl)-1,4-dihydro-2,6-dimethyl-5-nitropyridine-3-carboxylic acid are suspended in 40 ml of absolute tetrahydrofuran and treated with 12.5 mmol of carbonyldiimidazole. The suspension is then stirred for 30 minutes at room temperature and for 30 minutes at reflux temperature. A solution of 11 mmol of 4-(6-oxo-1,4,5,6-tetrahydropyridazin-3-yl)benzyl alcohol and 10 mg of sodium methylate in 10 ml of tetrahydrofuran is then added, and the mixture is heated to reflux for 3.5 hours. It is then evaporated, and the residue is taken up in methylene chloride, washed successively with 1N hydrochloric acid, 1N sodium hydroxide solution and water, dried with magnesium sulphate and evaporated. The residue crystallizes from a little i-propanol.

Melting point: 245° C.
Yield: 81% of theory

The following compounds according to the invention in the table can be obtained analogously to the preceding examples:

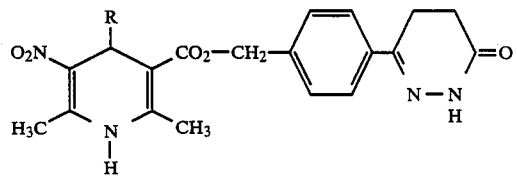

| No. | R | Melting point (°C.) |
|---|---|---|
| 4 | 2-CF₃-phenyl | 233 |
| 5 | 3-NO₂-phenyl | 270 |

-continued

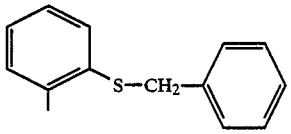

| No. | R | Melting point (°C.) |
|---|---|---|
| 6 | 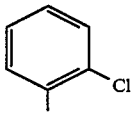 | 140 |
| 7 | 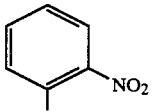 Cl | 264 |
| 8 | 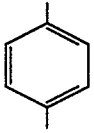 NO₂ | 254 |
| 9 | 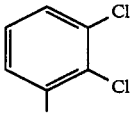 Cl | 234 |
| 10 | 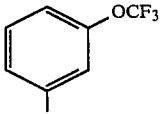 Cl, Cl | 257 |
| 11 | 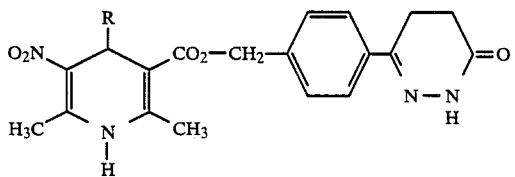 OCF₃ | 224 |

It will be understood that the specification and examples are illustrative but not limitative of the present invention and that other embodiments within the spirit and scope of the invention will suggest themselves to those skilled in the art.

We claim:

1. A 5-nitro-1,4-dihydropyridine of the formula

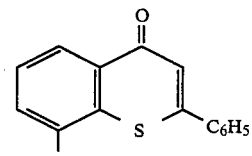

in which

R represents phenyl or naphthyl, which can be mono- to tetrasubstituted by identical or different substituents from the series comprising fluorine, chlorine, bromine, nitro, cyano, $C_1$-$C_4$-alkyl, $C_1$-$C_4$-alkoxy, $C_1$-$C_4$-alkylthio, trifluoromethyl, trifluoromethoxy, difluoromethoxy, trifluoromethylthio and benzyloxy or benzylthio optionally substituted by nitro, fluorine, chlorine, bromine, trifluoromethyl, methyl or methoxy, or respresents a heterocycle from the series thienyl, furyl, pyridyl, pyrimidyl, quinolyl, benzoxadiazolyl or thiochromenyl, optionally mono- to trisubstituted by methyl, fluorine, chlorine, bromine or phenyl, or represents straight-chain, branched or cyclic alkyl with up to 12 carbon atoms, or a physiologically acceptable salt thereof.

2. A compound or salt according to claim 1, in which

R represents phenyl, which can be mono- to trisubstituted by identical or different substituents from the series comprising fluorine, chlorine, nitro, cyano, $C_1$-$C_4$-alkyl, $C_1$-$C_4$-alkoxy, trifluoromethyl, trifluoromethoxy and benzyloxy or benzylthio optionally substituted by nitro, fluorine, chlorine, bromine, trifluoro-methyl, methyl or methoxy, or represents thienyl, furyl, pyridyl or benzoxadiazolyl, or represents a heterocycle of the formula

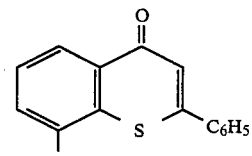

represents cyclic alkyl with up to 10 C atoms.

3. A compound according to claim 1, wherein such compound is 4-(6-oxo-1,4,5,6-tetrahydropyridazin-3-yl)benzyl 1,4-dihydro-2,6-dimethyl-4-(2-trifluoromethylphenyl)-5-nitropyridine-3-carboxylate of the formula

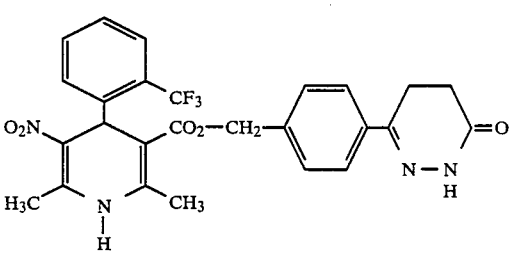

or a physiologically acceptable salt thereof.

4. A compound according to claim 1, wherein such compound is 4-(6-oxo-1,4,5,6-tetrahydropyridazin-3-yl)benzyl 1,4-dihydro-2,6-dimethyl-4-(3-nitrophenyl)-5-nitropyridine-3-carboxylate of the formula

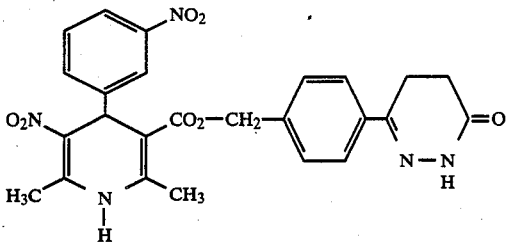

or a physiologically acceptable salt thereof.

5. A compound according to claim 1, wherein such compound is 4-(6-oxo-1,4,5,6-tetrahydropyridazin-3-yl)benzyl 1,4-dihydro-2,6-dimethyl-4-(2,3-dichlorophenyl)-5-nitropyridine-3-carboxylate of the formula

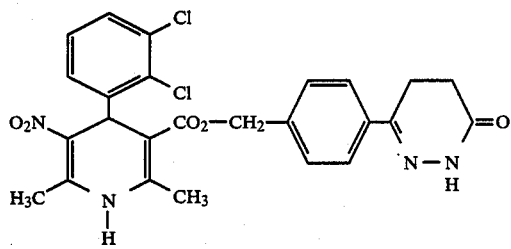

or a physiologically acceptable salt thereof.

6. A compound according to claim 1, wherein such compound is 4-(6-oxo-1,4,5,6-tetrahydropyridazin-3-yl)benzyl 1,4-dihydro-2,6-dimethyl-4-(2-methoxyphenyl)-5-nitropyridine-3-carboxylate of the formula

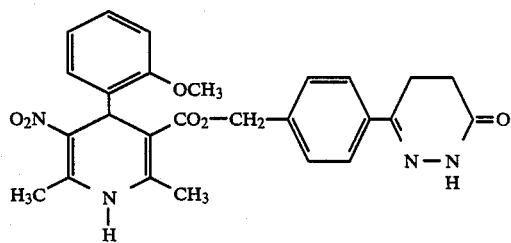

or a physiologically acceptable salt thereof.

7. A compound according to claim 1, wherein such compound is 4-(6-oxo-1,4,5,6-tetrahydropyridazin-3-yl)benzyl 1,4-dihydro-2,6-dimethyl-4-(2-benzyloxyphenyl)-5-nitropyridine-3-carboxylate of the formula

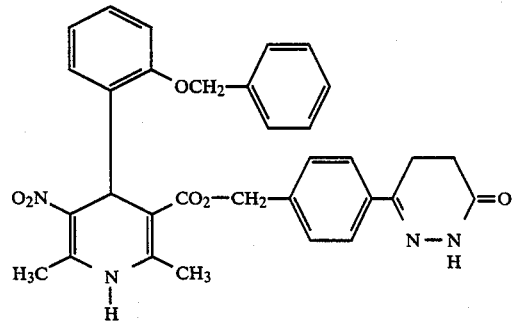

or a physiologically acceptable salt thereof.

8. A compound according to claim 1, wherein such compound is 4-(6-oxo-1,4,5,6-tetrahydropyridazin-3-yl)benzyl 1,4-dihydro-2,6-dimethyl-4-(2-p-fluorobenzylthiophenyl)-5-nitropyridine-3-carboxylate of the formula

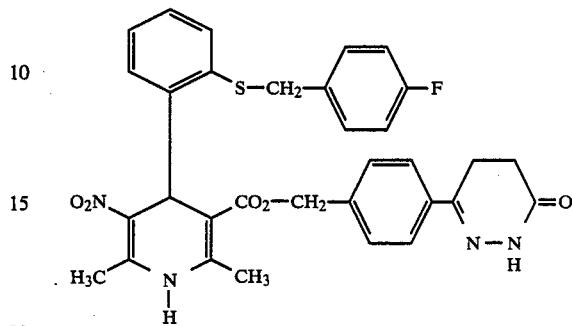

or a physiologically acceptable salt thereof.

9. A compound according to claim 1, wherein such compound is 4-(6-oxo-1,4,5,6-tetrahydropyridazin-3-yl)benzyl 1,4-dihydro-2,6-dimethyl-4-(2-m-trifluoromethylbenzylthiophenyl)-5-nitropyridine-3-carboxylate of the formula

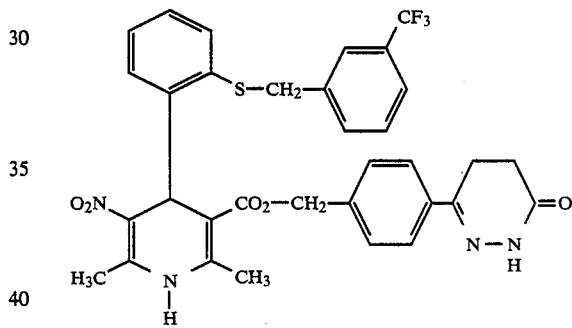

or a physiologically acceptable salt thereof.

10. A composition for increasing blood pressure or for the treatment of cardiac insufficiency or arrhythmia comprising an effective amount therefor of a compound or salt according to claim 1 and a diluent.

11. A unit dose of a composition according to claim 10 in the form of a tablet, capsule or ampoule.

12. A method of treating a patient for raising his blood pressure, for cardiac insufficiency or for arrhythmia which comprises administering to such patient an effective amount therefor of a compound or salt according to claim 1.

13. The method according to claim 12, wherein such compound is
4-(6-oxo-1,4,5,6-tetrahydropyridazin-3-yl)benzyl 1,4-dihydro-2,6-dimethyl-4-(2-trifluoromethylphenyl)-5-nitropyridine-3-carboxylate,
4-(6-oxo-1,4,5,6-terahydropyridazin-3-yl)benzyl 1,4-dihydro-2,6-dimethyl-4-(3-nitrophenyl)-5-nitropyridine-3-carboxylate,
4-(6-oxo-1,4,5,6-tetrahydropyridazin-3-yl)benzyl 1,4-dihydro-2,6-dimethyl-4-(2,3-dichlorophenyl)-5-nitropyridine-3-carboxylate,
4-(6-oxo-1,4,5,6-tetrahydropyridazin-3-yl)benzyl 1,4-dihydro-2,6-dimethyl-4-(2-methoxyphenyl)-5-nitropyridine-3-carboxylate, 4-(6-oxo-1,4,5,6-tetrahydropyridazin-3-yl)benzyl 1,4-dihydro-2,6-dimethyl-4-(2-benzyloxyphenyl)-5-nitropyridine-3-carboxylate, 4-(6-oxo-1,4,5,6-tetrahydropyridazin-3-yl)benzyl 1,4-dihydro-2,6-dimethyl-4-(2-p-fluorobenzylthiophenyl)-5-nitropyridine-3-carboxylate, or 4-(6-oxo-1,4,5,6-tetrahydropyridazin-3-yl)benzyl 1,4-dihydro-2,6-dimethyl-4-(2-m-trifluoromethylbenzylthiophenyl)-5-nitropyridine-3-carboxylate, or a physiologically acceptable salt thereof.

* * * * *